US008227262B2

(12) United States Patent
Fonnum et al.

(10) Patent No.: US 8,227,262 B2
(45) Date of Patent: *Jul. 24, 2012

(54) PROCESS FOR PREPARATION OF COATED POLYMER PARTICLES CONTAINING SUPERPARAMAGNETIC CRYSTALS

(75) Inventors: Geir Fonnum, Fjellhamar (NO); Lars Kilaas, Trandheim (NO); Arvid Trygve Berge, Trandheim (NO); Tom-Nils Nilsen, Ranheim (NO); Ruth Schmid, Tiller (NO); Grete Irene Modahl, Oslo (NO)

(73) Assignee: Invitrogen Dynal AS, Oslo (NO)

( * ) Notice: Subject to any disclaimer, the term of this patent is extended or adjusted under 35 U.S.C. 154(b) by 280 days.

This patent is subject to a terminal disclaimer.

(21) Appl. No.: 12/425,283

(22) Filed: Apr. 16, 2009

(65) Prior Publication Data

US 2009/0291506 A1    Nov. 26, 2009

Related U.S. Application Data

(63) Continuation of application No. 11/333,624, filed on Jan. 17, 2006, now abandoned.

(60) Provisional application No. 60/658,736, filed on Mar. 4, 2005.

(30) Foreign Application Priority Data

Jan. 17, 2005 (GB) ................................. 0500888.3

(51) Int. Cl.
*G01N 33/553* (2006.01)
*G01N 33/547* (2006.01)
*G01N 33/53* (2006.01)
*C12Q 1/68* (2006.01)

(52) U.S. Cl. ............. 436/526; 436/532; 435/7.1; 435/6; 435/7.92

(58) Field of Classification Search .................. None
See application file for complete search history.

(56) References Cited

U.S. PATENT DOCUMENTS

| 5,091,206 A | 2/1992 | Wang et al. |
| 5,648,124 A | 7/1997 | Sutor et al. |
| 5,736,349 A | 4/1998 | Sasaki et al. |
| 5,989,447 A | 11/1999 | Podszun et al. |
| 6,133,047 A | 10/2000 | Elaissari et al. |
| 6,986,913 B2 | 1/2006 | Fonnum et al. |
| 7,160,707 B2 | 1/2007 | Fonnum et al. |
| 2004/0014860 A1 | 1/2004 | Meier et al. |

FOREIGN PATENT DOCUMENTS

| CN | 1849512 | 10/2010 |
| JP | 2000-516345 | 12/2000 |
| WO | WO-90/10696 | 9/1990 |
| WO | WO-96/40502 | 12/1996 |
| WO | WO-03/005029 | 1/2003 |
| WO | WO-2004/053490 | 6/2004 |
| WO | WO-2005/015216 | 2/2005 |

OTHER PUBLICATIONS

U.S. Appl. No. 11/333,624, Non-Final Office Action mailed Oct. 16, 2008.
200680002458.4, First Office Action mailed Sep. 9, 2010.
200680002458.4, Response to Office Action mailed Sep. 9, 2010; filed Mar. 1, 2011.
06700598.3, Examination Report dated Mar. 3, 2008.
06700598.3, Response to Office Action dated Mar. 3, 2008.
06700598.3, Office Action mailed Jan. 28, 2009.
06700598.3, Response to Office Action mailed Jan. 28, 2009, Filed Oct. 6, 2009.

*Primary Examiner* — Shafiqul Haq

(57) ABSTRACT

A process for the preparation of coated polymer particles containing superparamagnetic crystals, said process comprising reacting surface-functionalized, superparamagnetic crystal-containing polymer particles of diameter less than 0.5 μm with at least one polyisocyanate and at least one diol.

33 Claims, No Drawings

PROCESS FOR PREPARATION OF COATED POLYMER PARTICLES CONTAINING SUPERPARAMAGNETIC CRYSTALS

CROSS REFERENCE TO RELATED PATENT APPLICATIONS

This is a continuation application and claims the right of priority under 35 U.S.C. §120 to U.S. application Ser. No. 11/333,624, filed Jan. 17, 2006, which claims the right of priority under 35 U.S.C. §119 to British Patent Application No. GB0500888.3 filed on Jan. 17, 2005, and to U.S. Provisional Patent Application Ser. No. 60/658,736 filed on Mar. 4, 2005, both of which are commonly owned with the present application, and both of which are hereby expressly incorporated by reference in their entirety as though fully set forth herein.

BACKGROUND OF THE INVENTION

1. Field of the Invention

This invention relates to a process for the preparation of coated magnetic polymer particles.

2. Description of the Related Art

Magnetic polymer particles are of general utility in various medical and biochemical fields, for example as transport vehicles for the delivery of pharmaceutical products, for diagnostic purposes, for separation and for synthetic purposes. Such particles rely upon their magnetic properties in order to perform these functions. In diagnostic assay applications, for example, application of a magnetic field to a sample containing an analyte bound to magnetic polymer particles allows the isolation of the analyte without the use of centrifugation or filtration and in therapeutic applications, for example, application of a magnetic field to the patient may serve to target drug-carrying magnetic polymer particles to a desired body site.

By magnetic is meant herein that the polymer particles contain superparamagnetic crystals. Thus the magnetic polymer particles are magnetically displaceable but are not permanently magnetizable. Many processes for preparing magnetic polymer particles are known, a large number of which involve preparing maghemite- or magnetite-containing polymer particles from pre-formed magnetic iron oxides, e.g. magnetite. Some of processes involved are described in U.S. Pat. No. 4,654,267 (Ugelstad) the contents of which are incorporated herein by reference.

With the development of devices which can measure very small changes in magnetism as well as the growth in nanotechnology it is envisaged that magnetic particle users will desire smaller particles with which to conduct their assays etc in the future. Moreover, the magnetic particles will need to be manipulated to carry reactive groups which can be readily coupled with labels to provide an ideal solid phase for biochemical procedures.

DETAILED DESCRIPTION OF THE INVENTION

We have now surprisingly discovered that magnetic particles with particularly useful surface characteristics may be produced by reacting surface functionalized, magnetic polymer particles with a combination of polyisocyanate/diol monomers to produce a "coated" magnetic polymer particle. Such particles are readily coupled further with labels to provide a solid phase support useful in a variety of fields.

Viewed from a first aspect, therefore, the invention provides a process for the preparation of coated polymer particles containing superparamagnetic crystals, said process comprising reacting surface-functionalized, superparamagnetic crystal containing polymer particles of diameter less than 0.5 μm with at least one polyisocyanate, e.g. diisocyanate, and at least one, preferably at least two, diols.

Preferred diols are polyethylene glycols or are of formula $HO((CH_2)_mO)_nH$ (where n is an integer of 1 to 15, e.g. 2 to 10, preferably 2 to 4, and m is an integer of 2 to 6, preferably 2 to 3, most preferably 2). Where only one diol is employed, this is preferably a polyethylene glycol, e.g. polyethylene glycol 300, 400, 500 or 600.

The polymer particles used in the process of the invention may be any suitably sized, optionally porous polymer particles having a functionalized surface, e.g. Ugelstad particles as generally described in U.S. Pat. No. 4,654,267. Suitable particles are also available from Ademtech, e.g. Carboxyl-Ademtech 0212 particles which comprise a carboxylic acid surface coating.

The surface functionality on the polymer particle is preferably a group capable, optionally with activation, of reacting with a polyisocyanate to covalently bond the polyisocyanate to the surface. Most preferably the surface is amine or carboxyl functionalized.

The polymer particle is preferably made from combinations of vinylic polymers, e.g. styrenes, acrylates and/or methacrylates. The polymeric material may optionally be crosslinked, for example by incorporation of cross-linking agents, for example as comonomers, e.g. divinylbenzene (DVB) or ethyleneglycol dimethacrylate. Particles comprising DVB are preferred.

Appropriate quantities of the cross-linking agents (e.g. comonomers) required will be well known to the skilled man. Preferably the polymer is a cross-linked styrenic polymer (e.g. a styrene-divinylbenzene polymer, which may be surface functionalized by the use of a nitro-group containing comonomer, e.g. nitro-styrene, and subsequent reduction) or a cross-linked (meth)acrylic polymer surface functionalized by the use of an epoxy-group containing comonomer (e.g. glycidylmethacrylate) and subsequent amination (e.g. by reaction with ethylene diamine).

The superparamagnetic crystals in the polymer particles used in the process of the invention may be of any material capable of being deposited in superparamagnetic crystalline form on the polymer particles or in the pores thereof should the particle be porous. Magnetic iron oxides, e.g. magnetite or maghemite are preferred; however the crystals may be of mixed metal oxides or other magnetic material if desired. The total quantity of crystalline magnetic material present is generally more than 20%, preferably more than 25%, desirably more than or equal to 30% (by weight, e.g. up to 85% wt or at least 50 wt %, e.g. 30 to 80 wt %. The percentage is calculated on a Fe (or equivalent metal in the case of magnetic materials other than iron oxides) weight basis based upon the overall dry weight of the coated particles.

Higher concentrations of magnetic crystals in the polymer particles are required for the small particles claimed herein so that they can be successfully attracted by a magnet during any isolation procedure. Another way of increasing the ease that beads are dragged towards a magnet is to make a portion of them remanent.

The degree of remanency may be measured by a vibrating sample magnetometer by running hysteresis curves. The curves are produced by measuring the magnetisation of the particles at different field strengths going from, for example, −1.5 tesla to +1.5 tesla and back. If the maximum magnetisation is called Ms and the absolute value of crossing the Y-axis (Zero Field strength) is called Mr, the ratio Mr/Ms will tell how remanent the particles are.

Particles with a ratio of Mr/Ms lower than 0.15 can for most application be considered superparamagnetic. The time interval for going from −1.5 to +1.5 tesla should be 10 minutes. Particles with low values of remanency often have increased drag towards a magnet because of aggregation, but the forces between them are so small that this do not influence sample washing.

Porous polymer particles may have magnetic particles deposited in their pores by standard techniques. As a further possibility, porous polymer particles may be prepared from nitro styrene and DVB, and magnetic material introduced. The use of amino styrene, particularly 4-aminostyrene, as monomer or comonomer in the preparation of amino-bearing polymeric material is preferred. Use of this monomer or comonomer obviates the need for post-polymerisation nitration and reduction reactions. Moreover, the more predictable nature (homogeneity) of the coating afforded by this process permits a more reliable coating to be applied.

The polymer particles may be formed carrying surface functionalisation or alternatively, functionalisation of the polymeric material may take place after polymerisation by, for example, nitration and subsequent reduction of the thus-formed nitro groups to pendant amine groups; or direct amination, for example by treatment with amino ethanol.

Polymer particles according to the present invention will have sizes (i.e. diameters) that are less than 500 nm, e.g. generally in the range from 100 nm to 400 nm, e.g. 150 nm to 250 nm.

Typically the particles used will have a surface area of at least 15 m5/g (measured by the BET nitrogen absorption method), and more preferably at least 30 m5/g, e.g. up to 700 m5/g, when corrected to a mean particle diameter of 2.7 μm (i.e. multiply surface area by 2.7/MD, where MD is the mean diameter in micrometers). Similarly scaled, the particle pore volume is preferably at least 0.1 mL/g.

Typically, the polymer particles are spherical and substantially monodisperse before they are coated and especially preferably remain spherical and substantially monodisperse once they have been coated.

By substantially monodisperse it is meant that for a plurality of particles (e.g. at least 100, more preferably at least 1000, e.g. all) the particles have a coefficient of variation (CV) of less than 20%, for example less than 15%, preferably less than 12%, more preferably less than 11%, still more preferably less than 10% and most preferably no more than about 8%, e.g. 2 to 5%. CV is determined in percentage as $$CV = \frac{100 \times \text{standard deviation}}{\text{mean}}$$

where mean is the mean particle diameter and standard deviation is the standard deviation in particle size. CV is preferably calculated on the main mode, i.e. by fitting a monomodal distribution curve to the detected particle size distribution. Thus some particles below or above mode size may be discounted in the calculation which may for example be based on about 90% of total particle number (of detectable particles that is). Such a determination of CV is performable on a Coulter LS 130 particle size analyzer.

The reaction of the magnetic polymer particle with the polyisocyanates generates a polymer coating. When the particles are porous, the resulting "coated" particles then have reduced porosity relative to the porous starting material. Surprisingly we have found that the superparamagnetic crystals appear to catalyse the polymerization so that the coating forms preferentially in their vicinity.

In another preferred embodiment, the coating polymer is formed from one or more (e.g. 1, 2 or 3) polyisocyanates and one or more (e.g. 2, 3 or 4) diols. Preferably, one polyisocyanate should be employed, e.g. one diisocyanate. Alternatively, a mixture of closely related polyisocyanates can be employed (e.g. Desmodur).

Typical polyisocyanates which may be used include methylene diisocyanate, hexamethylene diisocyanate, 2,4-toluene diisocyanate (2,4-TDI) (and isomers or mixtures thereof), isophorone diisocyanate (IPDI), 4,4'-oxybis(phenylisocyanate), 4,4'-diphenylmethane diisocyanate (MDI), mixtures of MDI and oligomers based on MDI (e.g. Desmodur VL), 2,4-diphenyldiisocyanate, methylene biscyclohexyl diisocyanate ($H_{12}$MDI), phenylene diisocyanate (p-PDI), trans-cyclohexane-1,4-diisocyanate (CHDI), 1,6-diisocyanatohexane (DICH), 1,5-diisocyanato-naphthalene (NDI), paratetramethylxylene diisocyanate (p-TMXDI) or metatetramethylxylene diisocyanate (m-TMXDI).

An especially preferred isocyanate is MDI or polyisocyanates based thereon (e.g. Desmodur). Desmodur comprises MDI and oligomers thereof comprising MDI with $CH_2$-phenylisocyanate residues. The Desmodur is thus a mixture of various polyisocyanates deriving from MDI. A sample structure may be 4,4-methylene bis(phenylisocyanate) 40-50%

4,4-methylene bis(phenylisocyanate)+benzylisocyanate: 20-25%

4,4-methylene bis(phenylisocyanate)+2 benzylisocyanate: 10%

4,4-methylene bis(phenylisocyanate)+3 benzylisocyanate: 2%.

(In a reaction like this the product also contains some of the 2-isomer). The compound is sold by Shell under the trade name Caradate and under the trade names Hylene and Rubinate by Huntsman.

Preferably two diols should be employed. The diols are preferably used in a molar ratio of 0.5:1 to 1:0.5, more preferably 0.8:1 to 1:0.8 when two diols are used. Preferably no one diol is used in a quantity exceeding 90% mol. of the diol mixture.

Preferred diols include diethylene glycol, tetraethylene glycol and polyethylene glycols e.g. PEG 300, 400 or 600. A preferred diol combination is diethylene glycol and tetraethylene glycol.

During the coating reaction involving the polyisocyanate, it is preferred if, in a first stage the polyisocyanate is in excess (e.g. relative to any diol). It is within the scope of the invention to use only polyisocyanate in this step of the coating procedure. This is believed to minimise the possibility of gelling occurring during the reaction. Where a large excess of polyisocyanate is employed in an initial coating reaction, it may then be necessary to react, in a second stage, the coated particles with further diol(s) (e.g. a diol as described above) to react with any unreacted isocyanate groups. Where the initial coating reaction uses polyisocyanate alone, it is essential that the resulting particle is reacted with at least one diol thereafter.

In such an embodiment, such a diol is preferably a polyethylene glycol. The long chain of the PEG diol allows the formation of a sizable linker between the particle coating surface and hence makes easier reaction with affinity ligands such as streptavidin.

It is thus within the scope of the invention to react the particles with polyisocyanate followed by diol, i.e. a stepwise process, to effect coating.

Typically therefore, the coating reaction may be effected by impregnating the porous magnetic polymer particle with the polyisocyanate and diol(s), e.g. using a solution of these (for example in an organic solvent such as methanol or diglyme) or by mixing a dispersion of the particles in an organic solvent with a liquid diol/polyisocyanate mixture. Sonication may be used to improve impregnation and the reaction may be accelerated by raising the temperature, e.g. to 50-100° C. Any solvent used may be extracted by application of sub-ambient pressure.

Generally, the uses to which magnetic polymer particles are put, e.g. their use as diagnostic tools, require an appropriate degree of electrophilicity in order that they may participate adequately in coupling and other reactions in aqueous systems prevalent in biological media.

Whilst the general polarity of the coatings is desirably electrophilic, certain coatings which contain hydrophobic moieties may be incorporated so as to tailor the degree of electrophilicity to that which is desired. In this way, the invention permits the provision of useful diagnostic and other tools having a wide range of polarities.

If desired the surfaces of the coated magnetic polymer particles may be further functionalised, e.g. by coupling a drug molecule, a reporter label (e.g. a chromophore, fluorophore, enzyme or radiolabel), or a ligand (e.g. an antibody or antibody fragment, a metal ion complexing agent, a member of a specific binding partner pair (e.g. biotin or streptavidin), an oligopeptide, an oligonucleotide, or an oligosaccharide).

Such coupling may be direct or indirect (and so may or may not involve the use of a coupling agent to form a linkage between the particle and the substance being coupled to it) and may be biodegradable or non-biodegradable. Biodegradable couplings may be desired if the magnetic polymer particles are to be used for the targeted release of an active compound. Accordingly after coating has been effected, the pendent groups of the coating may be manipulated to provide appropriate functionality (for example epoxy, hydroxy, amino etc. functionalities) for the attachment of such substances.

The functionalised coated magnetic particle may be bound to an affinity ligand the nature of which will be selected based on its affinity for a particular analyte whose presence or absence in a sample is to be ascertained. The affinity molecule may therefore comprise any molecule capable of being linked to a magnetic probe which is also capable of specific recognition of a particular analyte. Affinity ligands therefore include monoclonal antibodies, polyclonal antibodies, antibody fragments, nucleic acids, oligonucleotides, proteins, oligopeptides, polysaccharides, sugars, peptides, peptide encoding nucleic acid molecules, antigens, drugs and other ligands. Examples of suitable affinity ligands are available in the published literature and are well known. The use of further binding partners, secondary affinity ligands and linking groups which is routine in the art will not be discussed further herein although it will be appreciated that the use of such species with the particles of the invention is possible if desired.

Viewed from a further aspect the invention provides the use of particles of the invention in syntheses, extractions or assays, in particular in nucleic acid detection.

Introduction of vinyl groups polymerisable with, for example, an acrylic acid can also be achieved by reacting the coating surface with a compound such as methacrylic anhydride. For example, a coated particle which has reacted with a diol might carry hydroxyl functionalities which would react readily with methyl acrylic anhydride to allow the introduction of vinyl groups to the polymer surface.

As mentioned above, the nature of the external substance coupled to the particles may be selected on the basis of its ability to bind to a particular target material. Nucleic acid detection generally involves probing a sample thought to contain target nucleic acids using a nucleic acid probe that contains a nucleic acid sequence that specifically recognises, e.g. hybridises with, the sequence of the target nucleic acids, such that the nucleic acid affinity ligand and the target nucleic acids in combination create a hybridisation layer. Suitably functionalised particles of the invention, e.g. carrying streptavidin, are ideally suited for nucleic acid detection.

Biotinylated single strand oligonucleotide probes bound to streptavidin particles can be used to isolate sequence specific DNA. The biotinylated probes are bound to the particles by mixing the appropriate amount of particles with an excess of biotinylated probe. The particles/probe are then incubated with the DNA sample in a hybridisation buffer, e.g. SSPE or SSC, under conditions appropriate for the length and sequence of the probe and DNA. The excess and unwanted DNA is washed away utilizing the magnetic properties of the particles. The captured DNA can be detected/quantified by PCR etc.

Biotinylated double strand DNA fragments bound to streptavidin particles can be used to isolate DNA sequence specific binding proteins. The biotinylated DNA is bound to the particles by mixing the appropriate amount of particles with an excess of biotinylated DNA fragments. The particles/DNA are then incubated with the protein sample in a hybridisation buffer, under conditions appropriate for the protein under investigation. The excess and unwanted protein is washed away utilizing the magnetic properties of the particles. The captured protein can be eluted from the probe (by high salt, low salt, heat, low pH etc) for downstream applications and detection.

The target material may optionally be a material of biological or synthetic origin, e.g. it may be a molecule or a group of molecules, including for example antibodies, amino acids, proteins, peptides, polypeptides, enzymes, enzyme substrates, hormones, lymphokines, metabolites, antigens, haptens, lectins, avidin, streptavidin, toxins, poisons, environmental pollutants, carbohydrates, oligosaccharides, polysaccharides, glycoproteins, glycolipids, nucleotides, oligonucleotides, nucleic acids and derivatised nucleic acids, DNA, RNA, natural or synthetic drugs, receptors, virus particles, bacterial particles virus components, cells, cellular components, natural or synthetic lipid vesicles, polymer membranes, polymer services and particles and glass and plastic surfaces.

Where the particles of the invention are to be employed in immunoassays it has surprisingly been found that tosylation of the particles after coating results in particles which exhibit improved performance in immunoassays. Thus, in a preferred embodiment, particles carrying a coating can be tosylated, e.g. by reaction of the particles with tosylchloride in the presence of a base. The resulting tosylated coated particles are new and form a further aspect of the invention. By tosyl is meant a toluene-4-sulphonyl group.

Moreover, such tosylated species can be readily reacted with affinity ligands, e.g. streptavidin to form still further new particles.

Thus viewed from a further aspect, the invention provides coated polymeric particles, carrying superparamagnetic crystals, having a coating formed from at least one polyisocyanate and at least one diol, which is subsequently tosylated, e.g. by reaction with tosyl chloride and optionally then reacted with an affinity ligand, e.g. streptavidin.

Moreover, it has surprisingly been found that particles of the diameters claimed herein have a greatly increased capacity for binding compared to particles of greater size, e.g. 3 µm particles. It is envisaged that the binding capacity of the claimed particles is over 200% greater than that of larger particles allowing the use of considerably lower amounts particles in an assay procedure.

The particles of the invention are therefore of utility in adsorption/desorption processes analogously to the mechanisms in Reversed Phase chromatography or hydrophobic interaction chromatography. Reversed phase chromatography is a separation technique that utilises a hydrophobic adsorption interaction between a solute molecule (e.g. a protein) and an immobilised hydrophobic ligand (e.g. the surface of particles). This interaction is usually so strong that it can occur in solutions of low ionic strength and is broken by the use of organic solvents (e.g. acetonitrile). Reversed phase chromatography can be used to fractionate complex protein samples and for desalting protein samples. RPC is usually performed using a solid phase packed in to a column. The particles of the invention enable the technique to be performed without a column, without sample dilution and to be automated with high throughput.

Hydrophobic interaction chromatography (HIC) is a separation technique that utilises a hydrophobic adsorption interaction between a solute molecule (e.g. a protein) and an immobilised hydrophobic ligand (e.g. the surface of particles). This interaction is weaker than the interactions utilised during RPC and requires promotion by high salt concentrations. Consequently, decreasing salt concentrations can be used to break these adsorption interactions. HIC can be used to fractionate complex protein samples and for desalting protein samples. HIC is usually performed using a solid phase packed in to a column. The particles of the invention enable the technique to be performed without a column, without sample dilution and to be automated with high throughput.

The invention will now be described further by reference to the following example.

Example 1

Polyurethane Coating of 0.3 µm Magnetic Carboxylic Acid Particles 6.5 gram of a magnetic particles dispersion (0212x from Ademtech), with a dry content of 3.1% by weight were added to a reaction vessel and placed on a magnet. The water phase was removed from the particles and the particles were washed three times with 5 mL 0.01M sodium hydroxide, twice with 5 mL 0.01M hydrochloric acid, again with 0.01M sodium hydroxide and then with pure water. Further the particles were washed with methanol and transferred to diethyleneglycoldimethylether. The concentration of particles in diethyleneglycol dimethylether were adjusted to the original value of 3.1% by weight.

0.5 gram of diphenylmethane diisocyanate (Desmodur vl, Bayer) was added, and the reaction vessel were placed on a vortex with a heating block. The temperature was set to 80° C. for 20 hours. Infrared spectroscopy showed that the particles have attached urethane groups and isocyanate groups (wave number 1707 $cm^{-1}$ for C=O stretch and 2278 $cm^{-1}$ for the N=C=O stretch).

The particle dispersion from above were added 0.6 gram of polyethylene glycol 300 and heated to 80° C. for 1 hour. The particles were washed twice with 20 mL diethyleneglycol dimethylether and further six times with 20 mL methanol and then transferred to water (3×20 mL). Infrared spectroscopy showed that the polyethylene glycol were covalently attached to the particles by a reduction in the N=C=O stretch at 2278 $cm^{-1}$ and an increase in the ether groups at (1112 $cm^{-1}$ and 1071 $cm^{-1}$).

What is claimed is:

1. A process for the preparation of coated polymer particles containing superparamagnetic crystals, said process comprising reacting surface-functionalized, superparamagnetic crystal-containing polymer particles of diameter less than 0.5 µm with at least one polyisocyanate and at least one diol wherein said diol is a diol of formula $HO((CH_2)_mO)_nH$ (where n is an integer of 1 to 15 and m is an integer of 2 to 6).

2. A process as claimed in claim 1 wherein at least two diols are employed.

3. A process as claimed in claim 1 wherein said diol is a polyethylene glycol.

4. A process as claimed in claim 1 wherein said diols are diethyleneglycol and tetraethyleneglycol.

5. A process as claimed in claim 1 wherein said polyisocyanate comprises 4,4-methylene bis(phenylisocyanate) or a polyisocyanate comprising 4,4-methylene bis(phenylisocyanate) with $CH_2$-phenylisocyanate residues (Desmodur™).

6. A process as claimed in claim 1 wherein said polyisocyanate is a diisocyanate.

7. A process as claimed in claim 1 wherein said particles are, in a first stage, reacted with a mixture of said polyisocyanate and at least one diol in which the polyisocyanate is in a molar excess relative to the diol(s) and, in a second stage, subsequently reacted with at least one diol.

8. A process as claimed in claim 7 wherein two diols are used in the first stage of the reaction and one or two diols used in the second stage.

9. A process as claimed in claim 8 wherein diethyleneglycol and tetraethyleneglycol are used in both stages of the reaction.

10. A process as claimed in claim 1 wherein the particles are, in a first stage, reacted with said polyisocyanate in the absence of diol, and, in a second stage, reacted with at least one diol.

11. A process as claimed in claim 3 wherein one diol is employed and said diol is a polyethylene glycol, wherein the polyethylene glycol is selected from the group consisting of polyethylene glycol 300, 400, 500 and 600.

12. A process as claimed in claim 1 wherein the particles are amine functionalised.

13. A process as claimed in claim 1 wherein said surface-functionalized polymer particles are nitrated and reduced styrene-divinylbenzene polymer particles.

14. A process as claimed in claim 1 wherein the diameter of the polymer particles is between 150 and 250 nm.

15. A process as claimed in claim 1 in which said coated particle is subsequently tosylated.

16. A process as claimed in claim 1 wherein subsequent to the coating reaction, said particles are coupled to a drug molecule, reporter moiety or ligand.

17. A process as claimed in claim 16 wherein said ligand is a monoclonal antibody, polyclonal antibody, antibody fragment, nucleic acid, oligonucleotide, protein, oligopeptide, polysaccharide, sugar, peptide, peptide encoding nucleic acid molecule, antigen or drug.

18. A process as claimed in claim 17 wherein said ligand is streptavidin.

19. A particle obtained by the process of claim 1.

20. A method of using the particle as claimed in claim 19 in an assay the method comprising:

coupling the particle as claimed in claim 19 with an external substance to form a first complex of the particle bound to the external substance, wherein the external substance has the ability of bind to a target material of interest that is to be detected;

incubating the first complex with a sample containing or suspected to contain the target material of interest to form a second complex of target material bound to the particle bound to external substance; and separating the second complex from the remainder of sample, wherein formation of the second complex is indicative of the presence of the target material in the sample.

21. The method of claim 20 wherein the target material of interest that is to be detected is a nucleic acid and the assay is an nucleic acid detection assay.

22. The method of claim 20 wherein the formation of the second complex comprises binding of the first complex to the target material of interest by hydrophobic adsorption and the assay comprises an hydrophobic interaction chromatography or a reversed phase chromatography.

23. A process as claimed in claim 5 wherein said polyisocyanate comprising 4,4-methylene bis(phenylisocyanate) comprises a mixture of 4,4'-diphenylmethane diisocyanate (MDI) and a mixture of polyisocyanates derived from 4,4'-diphenylmethane diisocyanate (MDI) (Desmodur™).

24. A process as claimed in claim 5 wherein said polyisocyanate comprising 4,4-methylene bis(phenylisocyanate) comprises 4,4-methylene bis(phenylisocyanate) at about 40% to 50%, 4,4-methylene bis(phenylisocyanate) covalently attached to benzylisocyanate at about 20% to 25%, 4,4-methylene bis(phenylisocyanate) covalently attached to 2 benzylisocyanate at about 10% and 4,4-methylene bis(phenylisocyanate) covalently attached to 3 benzylisocyanate at about 2%.

25. A process as claimed in claim 5 wherein said polyisocyanate comprising 4,4-methylene bis(phenylisocyanate) comprises a mixture of 4,4'-diphenylmethane diisocyanate (MDI) and oligomers of 4,4'-diphenylmethane diisocyanate (MDI) (Desmodur™ VL).

26. A process as claimed in claim 6 wherein said diisocyanate is a 4,4'-diphenylmethane diisocyanate (MDI).

27. A process as claimed in claim 25, wherein said diisocyanate is a mixture of 4,4'-diphenylmethane diisocyanate (MDI) and a oligomers of 4,4'-diphenylmethane diisocyanate (MDI) (Desmodur™ VL).

28. A process as claimed in claim 6 wherein said diisocyanate is a 4,4-methylene bis(phenylisocyanate).

29. The method of claim 20 wherein the target material of interest that is to be detected is an antigen or an antibody and the assay is an immunoassay.

30. The method of claim 20 wherein the target material is a biomolecule.

31. The method of claim 20 wherein the target material is a synthetic material.

32. The method of claim 31, wherein the synthetic material is a toxin, a poison, an environmental pollutants, or a synthetic drug.

33. The method of claim 20, further comprising detecting the target material comprised in the second complex.

\* \* \* \* \*